United States Patent [19]

Otake et al.

[11] Patent Number: 5,382,733
[45] Date of Patent: Jan. 17, 1995

[54] PROCESS FOR PREPARING NAPHTHALENE OR DERIVATIVE THEREOF

[75] Inventors: Masayuki Otake; Akio Nakanishi, both of Yokohama, Japan

[73] Assignee: Mitsubishi Kasei Corporation, Tokyo, Japan

[21] Appl. No.: 34,343

[22] Filed: Mar. 19, 1993

[30] Foreign Application Priority Data

Mar. 27, 1992 [JP] Japan .................................. 4-100196

[51] Int. Cl.⁶ ................................................ C07C 5/31
[52] U.S. Cl. ..................................... 585/407; 585/410; 585/411; 585/418
[58] Field of Search ................. 585/407, 410, 411, 418

[56] References Cited

U.S. PATENT DOCUMENTS

| | | | |
|---|---|---|---|
| 2,795,574 | 6/1957 | Feller et al. | 502/325 |
| 3,255,209 | 6/1966 | Teplitz et al. | |
| 3,931,348 | 1/1976 | Taniguchi et al. | 585/411 |
| 4,210,603 | 7/1980 | Cihonski | 260/580 |

FOREIGN PATENT DOCUMENTS

| | | |
|---|---|---|
| 2164806 | 8/1972 | Germany . |
| 2329402 | 12/1973 | Germany . |
| 2364688 | 7/1974 | Germany . |
| 49-62453 | 6/1974 | Japan . |
| 52-47460 | 12/1977 | Japan . |
| 62-240631 | 10/1987 | Japan . |
| 4-210936 | 8/1992 | Japan . |
| WO90-06907 | 6/1990 | WIPO . |

Primary Examiner—Asok Pal
Attorney, Agent, or Firm—Oblon, Spivak, McClelland, Maier & Neustadt

[57] ABSTRACT

Disclosed herein is a process for preparing naphthalene or a derivative thereof, which comprises subjecting a benzene derivative having at least one substituted or non-substituted aliphatic hydrocarbon group and being capable of forming a naphthalene ring to cyclodehydrogenation in the presence of a zirconia catalyst containing chromium in an oxidized state.

13 Claims, No Drawings

PROCESS FOR PREPARING NAPHTHALENE OR DERIVATIVE THEREOF

BACKGROUND OF THE INVENTION

The present invention relates to a process for the preparation of naphthalene or a derivative thereof. More particularly, the present invention relates to an improvement of the process for preparing naphthalene or a derivative thereof by means of cyclodehydrogenation of a benzene derivative having at least one aliphatic hydrocarbon group.

For the preparation of naphthalene or a derivative thereof, a process is known in which a benzene derivative having at an appropriate position an aliphatic hydrocarbon group as a side chain with an appropriate carbon chain length and being capable of forming naphthalene or a derivative thereof is subjected to cyclodehydrogenation by using a catalyst wherein a noble metal such as platinum, palladium, etc., is carried on alumina or the like, to obtain the naphthalene or the derivative thereof of a corresponding structure (for example, Japanese Patent Publication (Kokoku) No. 52-47460 (1977)).

However, when the above-mentioned catalyst is used in the cyclodehydrogenation process, the cyclization yield is unsatisfactory and the cyclic hydrocarbons of a 5-member ring such as alkylindane or alkylindene having the same total number of carbon atoms as naphthalene or a derivative thereof obtained therefrom are formed as by-products. These by-products are difficult to separate from naphthalene or a derivative thereof, as their boiling point is close to that of naphthalene or a derivative thereof, so that it is difficult to obtain the objective product with high purity.

There is also known a process for preparing dimethylnaphthalene by using a chromium oxide-aluminum oxide based catalyst (Japanese Patent Application Laid-Open (Kokai) No. 49-62453(1974)). However, when this catalyst is used, the selectivity of dimethylnaphthalene or the conversion ratio of the starting material is unsatisfactory.

Recently, a catalyst composed of zirconia and an alkaline earth metal oxide has been proposed, and attention is drawn to its remarkably high naphthalene selectivity in comparison with the conventional noble metal carrying-type catalysts or chromium oxide-aluminum oxide based catalysts (Japanese Patent Application Laid-Open (Kokai) No. 62-240631(1987)).

According to the studies by the present inventors, however, the catalyst disclosed in Japanese Patent Application Laid-Open (Kokai) No. 62-240631 was still not well satisfactory and needed further improvement in respect of selectivity, too.

Naphthalene or a derivative thereof is industrially used in great quantities as, for example, a base material of polymers used as industrial materials. Therefore, as the preparation method of naphthalene or a derivative thereof, there is mostly employed a continuous reaction system which is suited for mass production of the intended substance. In the continuous reaction system, the difference in conversion and selectivity in one cycle of reaction greatly affects the yield of the intended product after a long-time continuous operation. Therefore, development of a process which is higher in conversion ratio and selectivity as much as possible, even by a few percent, than the conventional methods has been strongly desired.

As a result of strenuous studies for attaining the above requirement, it has been found that by using a zirconia catalyst containing chromium in an oxidized state, naphthalene or a derivative thereof can be obtained efficiently with a high conversion ratio and a high selectivity from a benzene derivative having at least one aliphatic hydrocarbon group as a side chain and being capable of forming a naphthalene ring. On the basis of this finding, the present invention has been attained.

SUMMARY OF THE INVENTION

In an aspect of the present invention, there is provided a process for preparing naphthalene or a derivative thereof, which comprises subjecting a benzene derivative having at least one substituted or non-substituted aliphatic hydrocarbon group and being capable of forming a naphthalene ring to cyclodehydrogenation in the presence of a zirconia catalyst containing chromium in an oxidized state.

DETAILED DESCRIPTION OF THE INVENTION

In the process of the present invention, a zirconia catalyst containing chromium in an oxidized state (hereinafter, also referred to as chromium-containing zirconia catalyst) is used as the catalyst for the cyclodehydrogenation. It is known that a zirconium catalyst containing chromium as an essential component as one of the chromium-containing zirconia catalysts can be used for the preparation of an aldehyde (Japanese Patent Application Laid-Open (Kokai) No. 4-21093(1992)).

The catalyst used in the present invention can be prepared by mixing a chromium compound which is convertible into chromia (chromium oxide) by calcination, with a powder or molding material of a zirconium compound and calcining the resultant mixture at a temperature of usually 250° to 800° C. As the zirconium compound, there can be used zirconia and the compounds such as hydroxides or salts of zirconium which is the precursor of zirconia. As the chromium compound, there can be used, for example, mineral acid salts such as chromium nitrate, chromium sulfate, etc.; organic acid salts such as chromium acetate, etc.; and organometallic complexes such as chromoacetyl acetonate, etc. The catalyst used in the present invention contains chromium in an oxidized state in an amount of preferably 0.5 to 25% by weight, more preferably 1 to 10% by weight (calculated as $Cr_2O_3$) based on zirconia. In the present invention, chromium in an oxidized state exists in the catalyst as chromia or as a composite oxide together with zirconia.

As typical examples of the catalyst preparation methods, there can be exemplified a process which comprises adding zirconium hydroxide powder to an aqueous solution of a chromium salt, mixing them, if necessary, in the presence of a binder, subjecting the resultant mixture to extrusion to obtain a molding material, drying the molding material and calcining it at a temperature of 250° to 800° C.; and a process which comprises adding zirconium hydroxide powder to an aqueous solution of a chromium salt, mixing them, evaporating the resultant mixture to dryness, calcining the resulting material at a temperature of 250° to 800° C., and tabletting the produced powder. As the binder in the above process, there can be used the commonly used binders such as polyvinyl alcohol.

The catalyst prepared in the manner described above may further contain, as an activity-modifying component, an alkali metal such as lithium, sodium, potassium, rubidium, cesium, etc.; an alkaline earth metal such as beryllium, magnesium, calcium, strontium, barium, etc.; and a transition metal such as gallium, indium, vanadium, molybdenum, lanthanum, cerium, nickel, cobalt, palladium, platinum and the like. The main effect of the metallic component is to prolong the catalyst life. The content of the metallic component is preferably not more than 5% by weight, more preferably 0.1 to 5% by weight based on the chromium-containing zirconia catalyst.

Said catalyst may be used singly, but it can also be used in combination with a known carrier such as silica, alumina, titania, aluminosilicate, diatomaceous earth or the like. The carrier may be added in the course of preparation of the catalyst, or it may be mixed with the catalyst after its preparation.

The catalyst or the catalyst-carrier mixture is molded into an appropriate shape and particle size according to the scale of the reaction, reaction system and other factors.

The average particle size of the catalyst, when used as a fixed bed, is usually 1 to 10 mm. The BET specific surface area of the catalyst is preferably 10 to 200 m$^2$/g.

The benzene derivative having at least one aliphatic hydrocarbon group and being capable of forming a naphthalene ring, which can be used as starting compound in the process of the present invention, are those which have at one or more appropriate position at least one aliphatic hydrocarbon group having an appropriate carbon chain length and are capable of forming a naphthalene ring upon undergoing cyclodehydrogenation. The aliphatic hydrocarbon group may be either straight or branched and may have a saturated or at least one unsaturated bond. Also, if necessary, the aliphatic hydrocarbon group may have at least one substituent group such as a carboxyl group, a formyl group, an acyl group, a hydroxyl group, an alkoxyl group or a halogen atom.

The benzene derivative having at least one aliphatic hydrocarbon group and being capable of forming a naphthalene ring, which are usable in the present invention, may be those having one aliphatic hydrocarbon group which has not less than 4, preferably 4 to 8, more preferably 4 to 6 of carbon atoms, or may be one having two or more aliphatic hydrocarbon groups, provided that two aliphatic hydrocarbon groups at the two adjacent positions of the benzene ring have not less than 4, preferably 4 to 8, more preferably 4 to 6 of the total number of carbon atoms in the longest linear chain portions.

When the aliphatic hydrocaron group is too long, it is apt to be cleaved from the benzene ring, resulting in a reduction of yield of the intended naphthalene or derivative thereof. Therefore, the carbon number of the aliphatic hydrocarbon group is preferably not more than 8, more preferably not more than 6.

In the present invention, it is preferred to use a benzene derivative represented by the following formula (I):

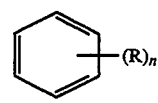

wherein each R represents independently a substituted or non-substituted aliphatic hydrocarbon group; the total number of carbon atoms in the longest linear chain portion of at least one —R or the total number of carbon atoms in the longest straight chain portions of two —R's at the adjacent positions of the benzene ring is not less than 4; the substituent of —R is a carboxyl group, a formyl group, an acyl group, a hydroxyl group, an alkoxyl group or a halogen atom; and n is an integer of 1 to 3.

Each —R is preferably independently an alkyl, alkenyl or alkadienyl group having 1 to 8 carbon atoms, more preferably an alkyl, alkenyl or alkadienyl group having 1 to 6 carbon atoms, provided that the total number of carbon atoms in the longest linear chain portion of at least one —R or the total number of carbon atoms in the longest straight chain portions of two —R's at the adjacent positions of the benzene ring is not less than 4.

Examples of —R include straight-chain aliphatic hydrocarbon groups such as methyl, ethyl, vinyl, propyl, propenyl, allyl, n-butyl, 1-butenyl, 2-butenyl, 3-butenyl, 1,3-butadienyl, n-pentyl, 1-pentenyl, 2-pentenyl, 3-pentenyl, 1,3-pentadienyl, n-hexyl, 1-hexenyl, 2-hexenyl, 3-hexenyl, 1,3-hexadienyl.

The substituent is preferably carboxyl group, formyl group, acyl group having 1 to 4 carbon atoms, hydroxyl group, alkoxyl group having 1 to 4 carbon atoms, or halogen atom.

Examples of the substituted aliphatic hydrocarbon group include branched aliphatic hydrocarbon groups having as side chains of said straight-chain aliphatic hydrocarbon groups the saturated or unsaturated aliphatic hydrocarbon groups such as methyl, ethyl, methylene, ethylidene, vinyl, etc., with the total carbon number of the branched aliphatic hydrocarbon group not exceeding 6.

Preferably, —R is a non-substituted aliphatic hydrocarbon group.

The total number of carbon atoms in the longest straight-chain portions of —R's is prefeably 4 to 8, more preferably 4 to 6.

n is preferably 1 or 2.

Among said aliphatic hydrocarbon groups, one in which the carbon atom associated with carbon-to-carbon bond which is newly formed in forming a ring is bonded to an adjacent carbon atom through a bond having π electrons, is preferred because the group facilitates the formation of napthalene ring. Examples of such groups include 3-butenyl, 1,3-butadienyl, 3-pentenyl, 1,3-pentadienyl, 3-hexenyl and 1,3-hexadienyl.

The aliphatic hydrocarbon group is properly selected in conformity to the structure of the intended naphthalene or derivative thereof. For example, in case where industrially useful dimethylnaphthalene is produced, it is recommended to select a benzene derivative in which n is 2, one —R si methyl group and an adjacent —R is 3-pentenyl group.

The cyclodehydrogenation reaction in the present invention is carried out by, for example, introducing the starting material in a gasified form singly or along with a carrier gas such as hydrogen, nitrogen, methane, water vapor, carbon dioxide, helium, argon or the like, into a reactor packed with said catalyst. This reaction is conducted in a gaseous phase under a pressure of usually 0.1 to 50 kg/cm$^2$, preferably 1 to 30 kg/cm$^2$, at a temperature of usually 250° to 750° C., preferably 300° to 750° C.

According to the process of the present invention, it is possible to produce the naphthalene or derivative thereof having the corresponding structure from the benzene derivative having at least one aliphatic hydrocarbon group at a higher conversion ratio and a higher selectivity than those when using the conventional catalysts.

The process of the present invention is especially advantageous for industrial mass production of a desired naphthalene or derivative thereof, because the yield in the one-cycle reaction according to the process of the present invention is higher by more than about 15% than that when using the conventional catalysts as seen from the Examples and the Comparative Examples described below.

EXAMPLES

The present invention will be described more particularly below with reference to the examples thereof, which examples however are merely intended to be illustrative and not to be construed as limiting the scope of the invention.

Reference Example 1 (Preparation of a catalyst used in the process of the present invention)

An aqueous solution composed of 325 g of chromium nitrate nonahydrate, 50 g of polyvinyl alcohol and 940 g of water were added to 2,340 g of zirconium oxyhydroxide, and the mixture was kneaded and extrusion molded into strings of 3 mm in diameter, and the molding was dried and calcined at 700° C. to prepare a catalyst. Thus obtained catalyst contained 3% by weight of chromium [calculated as chromium oxide (Cr$_2$O$_3$)] based on zirconia and had a BET specific surface area of 70 m$^2$/g. The catalyst was ground by a mortar and sieved to 10–20 meshes (JIS) for use in the reaction.

EXAMPLE 1

A pyrex glass-made reactor having an outer diameter of 20 mm was packed with 19 g of the catalyst prepared in Reference Example 1, with subsequent packing thereon with glass beads (3 mm in diameter).

Then, n-butylbenzene (a reagent produced by Tokyo Kasei K.K., purity: 99.5%) was supplied by a microfeeder. It was gasified in a nitrogen stream and introduced into the catalyst layer maintained at 550° C., at a liquid hourly space velocity (LHSV) of 0.045 to perform a cyclodehydrogenation in a gaseous phase for 4 hours. The conversion ratio of n-butylbenzene was 97.8%, and the yield of naphthalene was 97.0%.

EXAMPLE 2

Cyclodehydrogenation was carried out in the same way as Example 1 except that n-amylbenzene (a reagent produced by Tokyo Kasei K.K., purity: 98.9%) was used in place of n-butylbenzene, and that it was gasified in a nitrogen stream and introduced into the catalyst layer maintained at 550° C., at LHSV of 0.085. The conversion ratio of n-amylbenzene was 95.5%. Also, 1-methylnaphthalene was obtained at a selectivity of 72.1%, while naphthalene was obtained at a selectivity of 11.4%.

EXAMPLE 3

Cyclohydrogenation was carried out in the same way as Example 1 except that 5-o-tolylpentene-2 (purity: 99.8%) was used in place of n-butylbenzene, and that it was gasified in a nitrogen stream and introduced into the catalyst layer maintained at 500° C., at LHSV of 0.045. The convesion ratio of 5-o-tolylpentene-2 was 99.4%. Dimethylnaphthalenes (isomer mixture), ethylnaphthalene, methylnaphthalene and naphthalene were obtained at the selectivities of 16.0%, 8.2%, 4.1% and 2.1%, respectively. The total amount of said compounds having a naphthalene ring was 30.4 mol %.

Reference Example 2 (Preparation of zirconia catalyst)

A zirconia catalyst (ZrO$_2$: 100%) was prepared in the same way as Reference Example 1 except that no chromium nitrate solution was used.

Comparative Example 1

Cyclodehydrogenation of n-butylbenzene was carried out in the same way as Example 1 except that the zirconia catalyst prepared in Reference Example 2 was used in place of the catalyst prepared in Reference Example 1. The conversion ratio of n-butylbenzene was 96.6% and the selectivity of naphthalene was 84.3%.

Comparative Example 2

Cyclodehydrogenation of n-amylbenzene was carried out in the same way as Example 2 except that the zirconia catalyst prepared in Reference Example 2 was used in place of the catalyst prepared in Referential Example 1. The conversion of ratio n-amylbenzene was 64.1% and the selectivity of 1-methylnaphthalene was 60.2%.

Comparative Example 3

Cyclodehydrogenation of n-butylbenzene was carried out in the same way as Example 1 except that a platinum-carried alumina catalyst (Pt: 1%, ⅛ inch pellets produced by Nihon Engelhard) was used in place of the catalyst prepared in Reference Example 1. The conversion ratio of n-butylbenzene was 48.2% and the selectivity of naphthalene was 47.2%. The catalyst was deactivated rapidly and the conversion ratio dropped to 7% in 4 hours after start of the reaction.

Comparative Example 4

Aluminum oxide was immersed in an aqueous chromium nitrate solution, then dried and calcined at 700° C. in a nitrogen atmosphere for 3 hours to prepare a catalyst.

Cyclodehydrogenation of n-butylbenzene was carried out in the same way as Example 1 except that the above catalyst was used in place of the catalyst prepared in Reference Example 1. The conversion ratio of n-butylbenzene was 60.5% and the selectivity of naphthalene was 19.2%.

What is claimed is:
1. A process for preparing naphthalene or a derivative thereof, which comprises subjecting a benzene derivative having at least one substituted or non-substituted aliphatic hydrocarbon group and being capable of forming a naphthalene ring to cyclodehydrogenation in the presence of a catalyst consisting essentially of zirconia and chromium in an oxidized state, said cyclodehydrogenation being carried out in a gaseous phase, under a pressure of 0.1 to 50 Kg/cm$^2$ and at a temperature of 250° C. to 700° C.

2. A process according to claim 1, wherein said catalyst is one containing chromia.

3. The process according to claim 1, wherein an amount of chromium in an oxidized state is 0.5 to 25% by weight (calculated as Cr$_2$O$_3$) based on zirconia.

4. A process according to claim 1, wherein a BET specific surface area of said catalyst is 10 to 200 m$^2$/g.

5. A process according to claim 1, wherein said catalyst is obtainable by mixing a compound with a chromium compound and calcining the mixture.

6. A process according to claim 1, wherein the benzene derivative having at least one aliphatic hydrocarbon group and being capable of forming a naphthalene ring is the compound represented by the following formula (I):

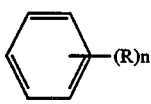
(I)

wherein each R represents independently a substituted or non-substituted aliphatic hydrocarbon group; (1) the total number of carbon atoms in the longest linear chain portion of at least one —R is not less than 4 or (2) if n is more than 1, at least two —R's are at adjacent positions of the benzene ring and the total number of carbon atoms in the longest straight chain portions of two —R's at the adjacent positions of the benzene ring is not less than 4; the substituent of —R is a carboxyl group, a formyl group, an acyl group, a hydroxyl group, an alkoxyl group or a halogen atom; and n is an integer of 1 to 3.

7. A process according to claim 6, wherein —R is an alkyl group, an alkenyl group or an alkadienyl group and has 1 to 8 carbon atoms.

8. A process according to claim 7, wherein —R has 1 to 6 carbon atoms.

9. A process according to claim 6 wherein at least one —R is 3-butenyl group, 1,3-butadienyl group, 3-pentenyl group, 1,3-pentadienyl group, 3-hexenyl group or 1,3-hexadienyl group.

10. A process according to claim 6, wherein n is 1 or 2.

11. A process according to claim 6, wherein the aliphatic hydrocarbon group is non-substituted.

12. A process according to claim 6, wherein the total number of carbon atoms in the longest straight chain portion of —R or in the longest straight chain portions of —R's is 4 to 6.

13. A process according to claim 6, wherein n is 2, one —R is methyl group, an adjacent —R is 3-pentenyl group, and the naphthalene derivative is dimethylnaphthalene.

* * * * *